(12) United States Patent
Zhang et al.

(10) Patent No.: US 12,685,510 B2
(45) Date of Patent: Jul. 21, 2026

(54) SPECTROSCOPIC PHOTOACOUSTIC IMAGING PROBE

(71) Applicant: Worcester Polytechnic Institute, Worcester, MA (US)

(72) Inventors: Haichong Zhang, Shrewsbury, MA (US); Shang Gao, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 18/667,740

(22) Filed: May 17, 2024

(65) Prior Publication Data

US 2024/0299009 A1 Sep. 12, 2024

Related U.S. Application Data

(63) Continuation-in-part of application No. 17/994,788, filed on Nov. 28, 2022, now Pat. No. 12,471,952, (Continued)

(51) Int. Cl.
A61B 17/00 (2006.01)
A61B 5/00 (2006.01)
(Continued)

(52) U.S. Cl.
CPC .......... A61B 8/4461 (2013.01); A61B 5/0095 (2013.01); A61B 8/12 (2013.01); (Continued)

(58) Field of Classification Search
CPC ... A61B 17/3403; A61B 8/085; A61B 8/4281; A61B 8/4444; A61B 2017/3413; A61B 8/0833; A61B 8/0841
See application file for complete search history.

(56) References Cited

U.S. PATENT DOCUMENTS

2003/0015037 A1 1/2003 Stephens et al.
2003/0199765 A1 10/2003 Stetten et al.
(Continued)

FOREIGN PATENT DOCUMENTS

EP 3426159 A1 1/2019
WO 2017139728 A1 8/2017
(Continued)

OTHER PUBLICATIONS

Extended European Search Report, EP 20 88 3393, Oct. 11, 2023, pp. 1-11.
(Continued)

*Primary Examiner* — Amal Aly Farag
(74) *Attorney, Agent, or Firm* — Armis IP Law, LLC

(57) ABSTRACT

A photoacoustic (PA) sensor employs a linear deployment of an illumination source and a corresponding ultrasonic receiver for defining an imaging plane for rendering a PA image of a surgical or diagnostic region. A pair of illumination sources emanates from cladding removal of respective optical fibers, and irradiates in alignment with a side firing ultrasonic (US) array for receiving the induced PA signals. The US array extends longitudinally and parallel to the illumination sources, and an overlap of the respective irradiation regions extends from the illumination sources lies within a sensing region of the US array for defining an imaging plane captured by the US sensor for rendering on a visual device, often in conjunction with an ablation antenna or diagnostic probe for providing concurrent imaging during a surgical procedure.

20 Claims, 10 Drawing Sheets

Related U.S. Application Data which is a continuation-in-part of application No. 17/083,776, filed on Oct. 29, 2020, now Pat. No. 11,627,933.

(60) Provisional application No. 63/467,511, filed on May 18, 2023, provisional application No. 63/077,340, filed on Sep. 11, 2020, provisional application No. 62/927,967, filed on Oct. 30, 2019.

(51) Int. Cl.

| | |
|---|---|
| *A61B 8/00* | (2006.01) |
| *A61B 8/12* | (2006.01) |
| *A61B 18/14* | (2006.01) |
| *A61B 90/00* | (2016.01) |

(52) U.S. Cl.
CPC .......... *A61B 8/445* (2013.01); *A61B 18/1492* (2013.01); *A61B 2017/00106* (2013.01); *A61B 2090/3782* (2016.02)

(56) References Cited

U.S. PATENT DOCUMENTS

| | | |
|---|---|---|
| 2008/0154257 A1 | 6/2008 | Sharareh et al. |
| 2009/0105597 A1 | 4/2009 | Abraham |
| 2011/0096629 A1 | 4/2011 | Raphael |
| 2011/0098572 A1 | 4/2011 | Chen et al. |
| 2012/0259204 A1 | 10/2012 | Carrat et al. |
| 2014/0180031 A1* | 6/2014 | Anderson ............... A61B 8/06 600/478 |
| 2018/0296194 A1 | 10/2018 | Yamanaka et al. |
| 2018/0311074 A1 | 11/2018 | Heeren |
| 2018/0360322 A1* | 12/2018 | Nagae .................. A61B 5/0095 |
| 2019/0076119 A1 | 3/2019 | Yang et al. |
| 2021/0353359 A1 | 11/2021 | Cook et al. |

FOREIGN PATENT DOCUMENTS

| | | |
|---|---|---|
| WO | 2017156023 A1 | 9/2017 |
| WO | 2017205808 A1 | 11/2017 |

OTHER PUBLICATIONS

International Search Report, PCT/US2020/057892, Feb. 18, 2021, pp. 7.
Yuusuke Tanaka, et al., "Basic Properties of an Ultrasonic Probe with a Through Hole for Puncture and Detection Principle of a Puncture Needle", Electronics and Communications in Japan, Wiley-Blackwell Publishing, Inc., US, vol. 97, No. 6, May 8, 2014, pp. 67-73. XP072449625.
International Search Report, PCT/US2024/030027, Sep. 5, 2024, pp. 1-8.
Leonardo G Montilla et al., "Real-time photoacoustic and ultrasound imaging: a simple solution for clinical ultrasound systems with linear arrays", Phys. Med. Biol. 58 (2013), pp. N1-N12, 2012, 12.06.

* cited by examiner

PA Probe Shaft

Side-firing US Probe

Directional Diffusing Fiber

US Imaging Plane

Fiber Illumination Distribution 130-2

120

131

132

152

110

130-1

134-1

134-2

SPECTROSCOPIC PHOTOACOUSTIC IMAGING PROBE

RELATED APPLICATIONS

This patent application claims the benefit under 35 U.S.C. § 119(e) of U.S. Provisional Patent App. No. 63/467,511, filed May 18, 2023, entitled "SPECTROSCOPIC PHO-TOACOUSTIC IMAGING PROBE," and is a Continuation in Part (CIP) of U.S. patent application Ser. No. 17/994,788, filed Nov. 28, 2022, entitled "ULTRASONIC IMAGING DEVICE." which is a continuation-in-part (CIP) under 35 U.S.C. § 120 of U.S. patent application Ser. No. 17/083,776, now U.S. Pat. No. 11,627,933, filed Oct. 29, 2020, entitled "RING-ARRAYED ULTRASONIC IMAGING," which claims the benefit under 35 U.S.C. § 119(e) of U.S. Provisional Patent App. No. 62/927,967, filed Oct. 30, 2019, entitled "RING-ARRAYED ULTRASONIC IMAGING," and on U.S. Provisional Patent App. No. 63/077,340, filed Sep. 11, 2020, entitled "INSERTION SITE ULTRASONIC IMAGING," all incorporated herein by reference in entirety

STATEMENT OF FEDERALLY SPONSORED RESEARCH AND DEVELOPMENT

This invention was made with government support under grant No. DP5 OD028162, awarded by the National Institute of Health. The Government has certain rights in the invention.

BACKGROUND

Ultrasonic sensors use sound waves, typically above the 20 KHz range, to detect objects in proximity. The ultrasound medium avoids harmful emissions such as x-rays and is more compact than Magnetic Resonance Imaging (MRI), hence can be portable. Other common uses include the automotive space, where ultrasonic sensors are prevalent for ADAS (Advanced Driver-Assistant Systems) applications, specifically for parking assist where perimeter-located sensors are used to detect obstacles when parking a vehicle. In the industrial space, ultrasonic sensors are used in robotics and other applications that require reliable presence, proximity, or position sensing.

Ultrasonic sensors can measure distance and detect the presence of an object without making physical contact, by producing and monitoring an ultrasonic echo. Detection in variances in object density can also be used for medical imaging to depict different tissue regions based on varied density. Depending on the sensor and object properties, an effective range in air is between a few centimeters up to several meters. The ultrasonic sensor (or transducer) generates and emits ultrasonic pulses that are reflected back towards the sensor by an object that is within the sensory field and range.

Photoacoustic (PA) imaging is an emerging biomedical imaging modality based on laser-generated ultrasound (US) providing high-resolution, real-time functional information of anatomy. PA imaging has been well-investigated in various applications including vascular mapping, blood oxygenation mapping, tumor detection, ablation monitoring as well as catheter tracking. The imaging modality has been demonstrated for guiding procedures (cardiac ablation, prostatectomy, hysterectomy, etc.) intraoperatively.

SUMMARY

A photoacoustic (PA) sensor employs a linear deployment of an illumination source and a corresponding ultrasonic receiver (sensor) for defining an imaging plane for rendering a PA image of a surgical or diagnostic region. A pair of illumination sources emanates from cladding removal of respective optical fibers, and irradiates in alignment with a side firing ultrasonic (US) array for receiving the induced PA signals. The US array extends longitudinally and parallel to the illumination sources, and an overlap of the respective irradiation regions extending from the illumination sources lies within a sensing region of the US array for defining an imaging plane captured by the US sensor for rendering on a visual device, often in conjunction with an ablation antenna or diagnostic probe for providing concurrent imaging during a surgical procedure.

Configurations herein are based, in part, on the observation that PA imaging mediums are often used for both diagnostic examination of anatomical regions as well as concurrent visualization of surgical regions for surgical instrument guidance. PA imaging systems are portable, as are their ultrasound counterparts, but can provide a greater range in return signals for distinguishing distinct tissue density and regions. Unfortunately, conventional approaches to PA imaging employ a convergence of light from multiple external points, limiting the imaged region or area by the intersection of the light beams. Accordingly, configurations herein substantially overcome the shortcoming of conventional PA probes by providing miniature, linear illumination sources adapted for internal deployment for providing an overlapping light irradiation region aligned with a linear sensory array of US sensors for sensing an imaging plane, rather than a single point or intersection of narrow beams projected from bulky sources.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations herein depict example configuration of a PA device for capturing image information in the imaging plane defined by an overlap of the sensing region of the US array and the irradiation region for each illumination source.

PA imaging receives image information in an acoustic signal similar to an US sensor, but the PA medium induces or generates the acoustic signal differently. US sensing emits and receives the acoustic signal from the same transducer, which both emits and received the US signal. The PA approach induces an acoustic return signal by an irradiating light signal, rather than an acoustic/sound signal.

In photoacoustic (PA) imaging, ultrasound waves are produced by irradiating the tissue with modulated electromagnetic radiation, usually pulsed on a nanosecond timescale. In the case of optical excitation, absorption by specific tissues such as hemoglobin, melanin, or water followed by rapid conversion to heat produces a small temperature rise. This rise of temperature (i.e., thermal expansion) leads to an initial pressure increase, which then subsequently relaxes, resulting in the emission of broadband low-amplitude acoustic waves. The acoustic waves propagate through the tissue to the surface, where they are detected by the ultrasound receiver. By measuring the time of arrival of the acoustic waves and knowing the speed of sound in tissue, a PA image can be reconstructed in the same way that a pulse-echo ultrasound image is formed. The acoustic pressures in PA are several orders of magnitude smaller than that in ultrasound.

In an US medium, an image represents the acoustic impedance mismatch between different tissues. A PA image, however, is absorption-based. It represents the initial pressure distribution produced by the deposition of the optical energy, which depends on the optical absorption and scattering properties of the tissue. PA imaging can provide greater tissue differentiation and specificity than ultrasound because the difference in optical absorption of tissues can be much larger than the difference in acoustic impedance. PA imaging thus provides the ability to distinguish structures having a higher optical absorption than surrounding tissue, some examples are blood vessels and nerves.

Figure 1:
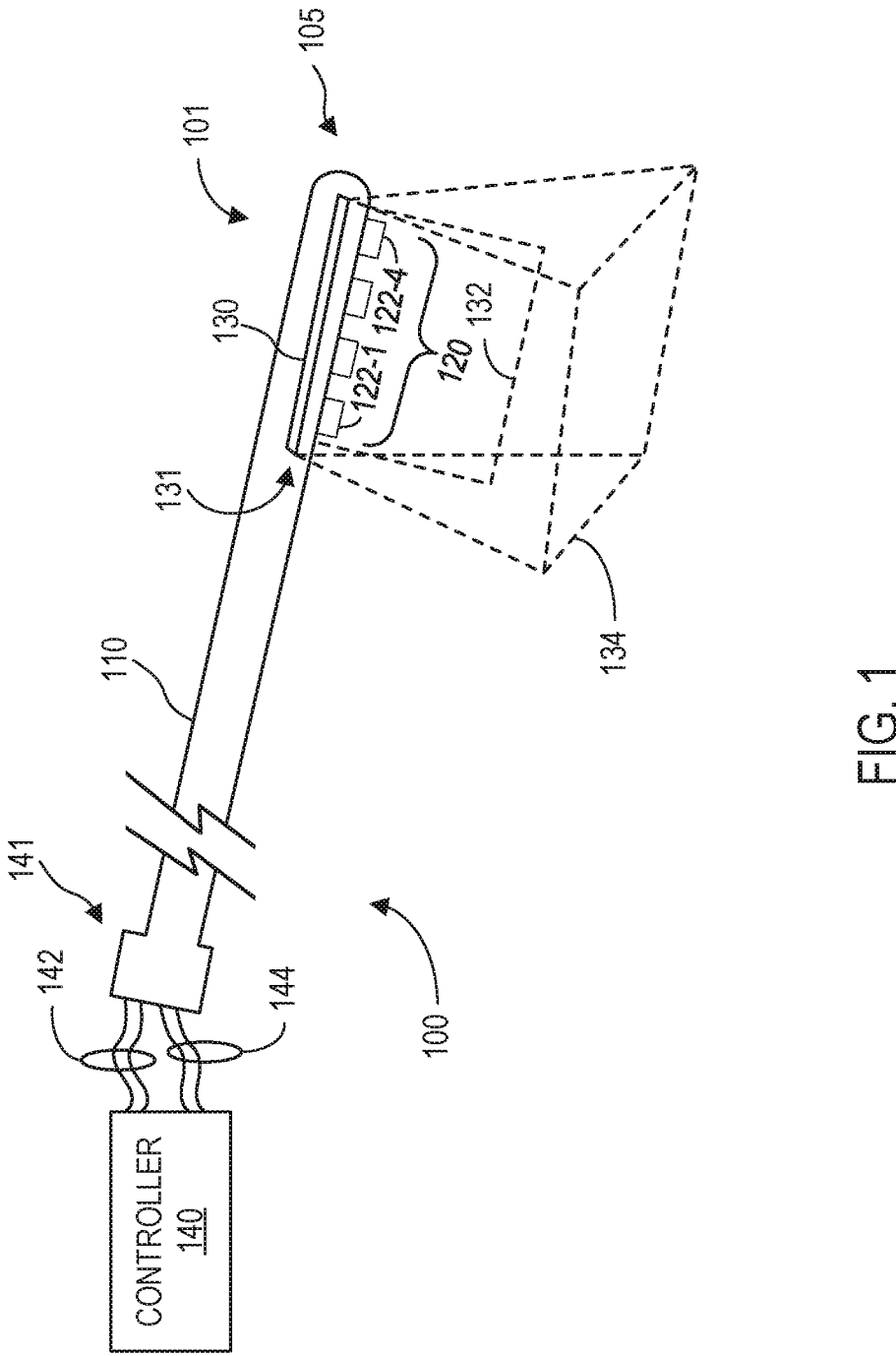
FIG. 1 is a context diagram of a photoacoustic (PA) environment suitable for use with configurations herein.

FIG. 1 is a context diagram of a photoacoustic (PA) environment suitable for use with configurations herein. Referring to FIG. 1, in the PA environment 100, an elongated probe 110 includes a sensing region 101 at a distal end 105 of the probe 110. The probe 110 is generally elongated and having a circular cross section for insertion to a surgical region. An ultrasonic array 120 includes a plurality of individual transducer elements 122-1 . . . 122-4 (122 generally) in a linear sequence or two dimensional array forming a rectangular arrangement with a length running parallel to an axis of the probe 110. One or more illumination sources 130 is also longitudinally extended for irradiating a sensing region 132 within an irradiation region 134 fanning out from a linear origin defined by the illumination source.

In the example configuration, the ultrasonic sensor is a side firing ultrasonic array 120 at the distal end 105 of the probe 110 and is aligned with the irradiation region 134 emanating from one or more illumination source 130. The side firing ultrasonic array 120 forms a sensing region 132 extending perpendicularly from the probe 110 for forming an imaging plane based on an intersection of the sensing region 132 and the respective irradiation regions 134.

A controller 140 connects to the illumination source 130 via optical fiber(s) 142, and also connects to the sensor array 120 via wires 144, for coordinating control of the illumination source 130 and receiving corresponding acoustic signals from tissue or objects in the sensing region 132. Based on alignment of the illumination source irradiating the sensing region 132 with the linear sensor array 120, along with precise timing of the illumination and reception of the induced acoustic waves, an imaging plane may be rendered indicative of a surgical or imaged region.

In conventional PA imaging instruments, a PA imaging probe is includes external laser energy delivery sources and an US transducer. Despite the acoustic signal's ability to penetrate deeper tissue, substantial optical attenuation limits the use of PA imaging for surgical guidance. To excite the PA signal, fiber bundles are frequently utilized as the most common optical components for delivering light energy. The fiber head is aligned with the US sensing array on one or two sides, and at a certain angle to maximize the light density at the desired imaging depth of approximately 30-40 mm. While this method ensures high imaging contrast on shallower areas, fiber bundles are unsuitable for imaging deeper tissue regions or organs for diagnosis or surgical guidance. Fiber bundles are typically bulky in size, making it difficult to penetrate the body without causing significant trauma to the patient. In other words, conventional light/laser sources are too large for anatomical insertion. Angle tips are sometimes used, but still employ the bulky fiber bundle. With the availability of minimally invasive surgery for many procedures, it would be beneficial to provide miniaturized PA light delivery systems as disclosed herein.

Figure 2A:
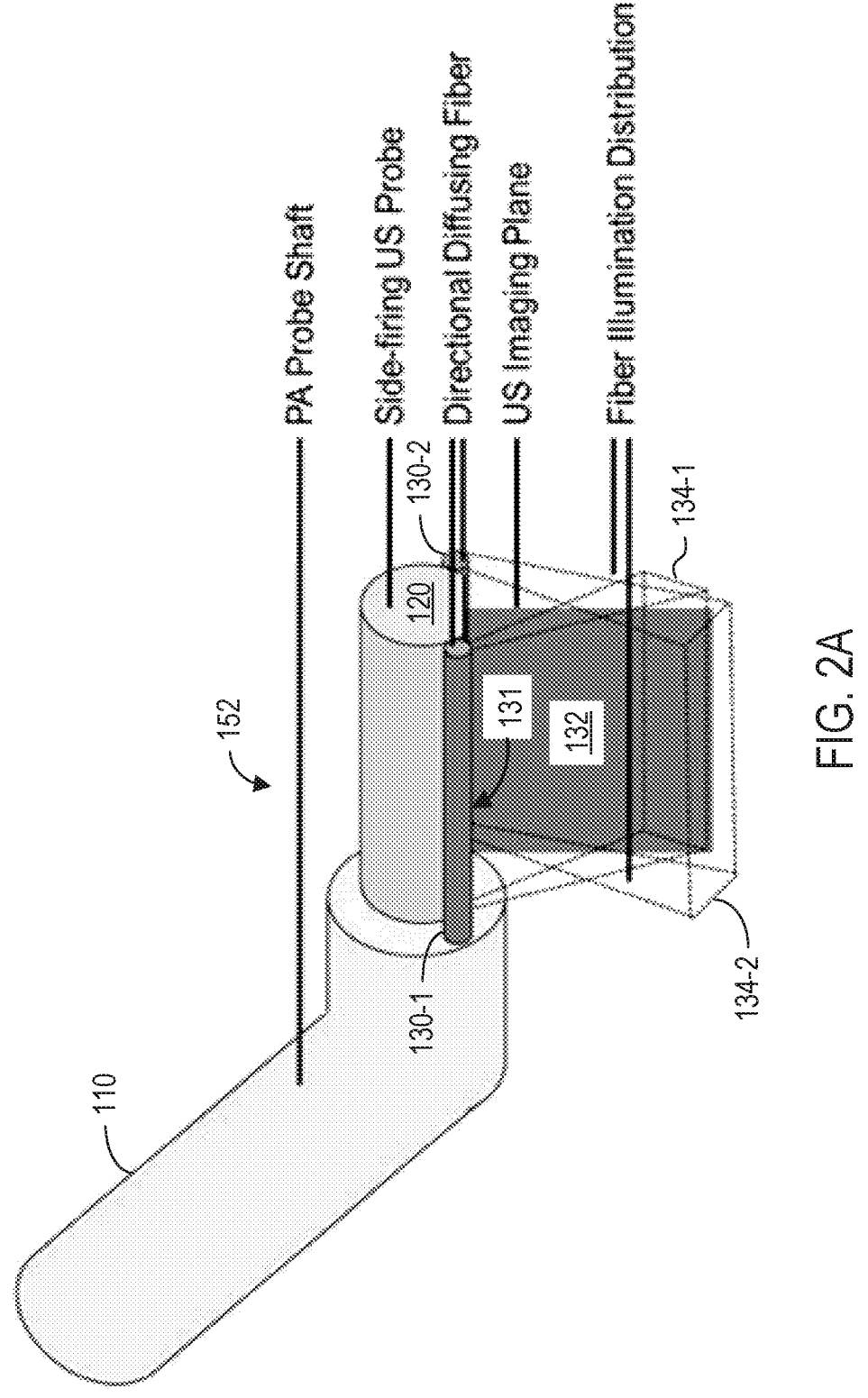
FIGS. 2A and 2B show a perspective view and front elevation view, respectively, of a PA probe in the environment of FIG. 1.
Figure 2B:
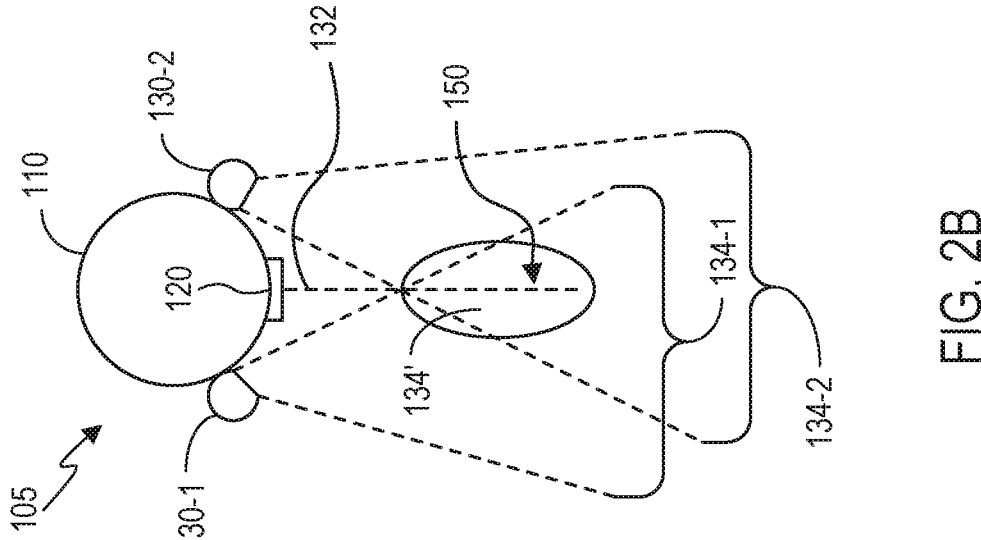

FIG. 2A is a perspective view of a PA probe in the environment of FIG. 1, and FIG. 2B is a front elevation facing the distal end of the probe. The use of diffusing fibers, defined by individual optical fibers irradiating a linear region, delivers illumination for PA excitation in a miniature form factor adapted for insertion to the surgical site. Diffusing fibers can illuminate a wider region than the same number of angled-tip side illumination fibers. Thus, an integrated PA imaging device with a miniaturized diameter and simplified alignment mechanism can provide intraoperative guidance with a flexible imaging angle, as shown in FIG. 2A. The imaging probe can be a stand-alone or integrated to be the part of robotics arms of a surgical system.

Referring to FIGS. 1 and 2A-2B, a particular configuration of the photoacoustic imaging device is shown. The PA probe 110 takes the form of a shaft, typically flexible, housing the optic fiber(s) 142 and wires 144. The wires 144 connect to the ultrasonic sensor 120, which extends longitudinally for forming a linear sensing area 131, defining the sensing region 132 from a rectangular region extending from the linear sensing area 131 formed from the array of sensors 122-N and perpendicular from an axis of the shaft. One or more (typically 2) illumination sources 130-1 . . . 130-2 (130 generally), flank the sensor 120, slightly below a diameter of the shaft, extending longitudinally for irradiating the region aligned with the linear sensing area. Each illumination source 130-N irradiates in an irradiation region 134-N.

At a proximal end 141, the controller 140 connects to the illumination source 130 for pulsed illumination of the illumination source and for corresponding reception of acoustic signals by the ultrasonic sensor 120. An imaging plane 150 is defined by the intersection of the sensing region 132 and all of the overlapping irradiation regions 134-N formed from the respective illumination sources 130. 'In the example configuration, the illumination sources 130 are defined by diffusion fibers formed at distal ends of optical fibers 142 terminating at the distal end 105.

FIGS. 2A and 2B illustrate a plurality of illumination sources 130-N, such that each illumination source of the plurality of illumination sources extends in parallel adjacent the liner sensing area 131 for defining an intersecting irradiation region 134' emanating from the parallel illumination sources 130. The natural "fan out" of the illumination sources forms the intersection. The sensing region 132 of the US sensor also meets this intersecting irradiation region 134'. The ultrasonic sensor 120 is responsive to an imaging plane 150, defined by a region parallel to the linear sensing area 131 and extending perpendicular to the longitudinal extension of the ultrasound sensor 120, and within the intersecting irradiation region 134' resulting from irradiation of light from each of the respective illumination sources 130.

The collective assembly forms a photoacoustic bundle 152, defined by the plurality of illumination sources 130 formed from diffusion fibers flanking the ultrasonic sensor 120, such that each of the diffusion fibers terminates in a respective illumination source 130-N, and thus the imaging plane 150 is defined by an intersection of the irradiation regions 134 extending from each of the illumination sources 130 and the sensing region 132 of the ultrasonic sensor 120.

As a practical matter, the probe 110 is elongated for extension into a surgical region, where the imaging plane 150 passes through the surgical region for imaging thereof. In various contexts, the probe may have a diameter of around 4 mm, suited for insertion into a borehole of around 12-14 mm or a laparoscopic incision. The probe 110 and bundle 152 may also be deployed with other instruments, such as an ablation antenna, other probe or surgical/laparo-scopic apparatus. By disposing in or adjacent the surgical region, the ultrasonic sensor 120 is responsive to changes in tissue density of the surgical region resulting from at least one of a vasculature, a tumor or necrosis, for example.

Figure 3:
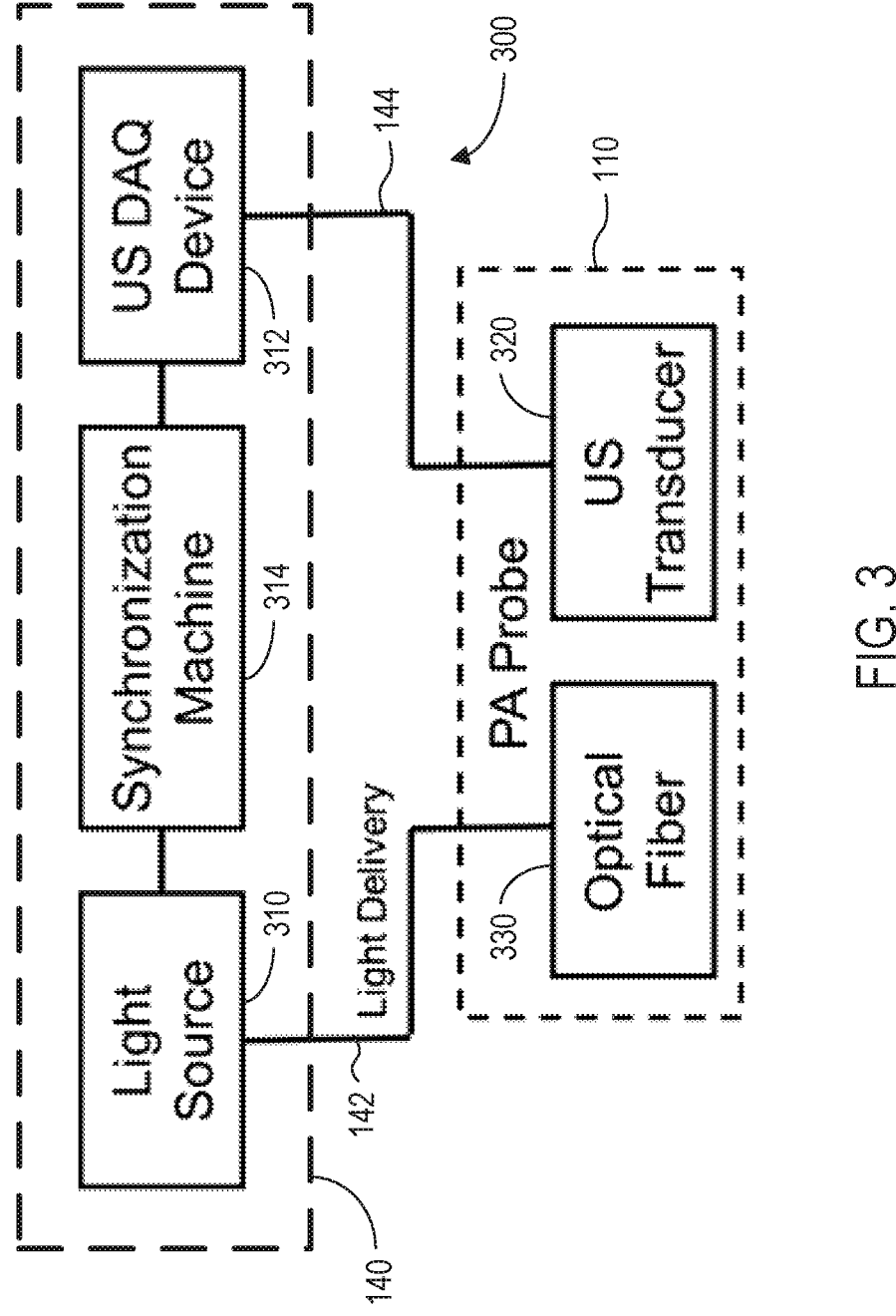
FIG. 3 is a block diagram of a controller for use with the probe of FIG. 2A.

FIG. 3 is a block diagram of a controller for use with the probe of FIGS. 2A and 2B. Referring to FIGS. 1-3, a photoacoustic (PA) imaging system 300 including the probe 110 is typically comprised of three primary components: a light source 310, a US data acquisition (DAQ) device 312, and a sensor actuation device 314. Various light sources may be employed, such as high-power pulsed laser, pulsed laser diode, LED, and continuous wave (CW) laser diode, with light either directly illuminated or coupled through a light delivery mechanism, such as optical fiber 142, as described above. Multiple types of optical fibers, including fiber bundles, tip-illumination fibers, and diffusing fibers, may be implemented for PA light delivery. While a linear array US probe 110 is the most commonly selected US transducer, other designs that utilize various US transducers, such as phased array US probes and laparoscopic US probes, are also adaptable to a PA system.

The controller 140 coordinates light pulses from the illumination source 130 at a particular frequency so as to induce the rapid heat-induced expansion of tissue in the image plane 150. The resulting rapid expansion and con-traction results in acoustic signals received by the US array 120, which are interpreted by the DAQ logic/processing 312 for determining the timing and propagation from illumina-tion excitation and heating to compute density of tissue, and more importantly, differences in tissue density.

Figure 4A:
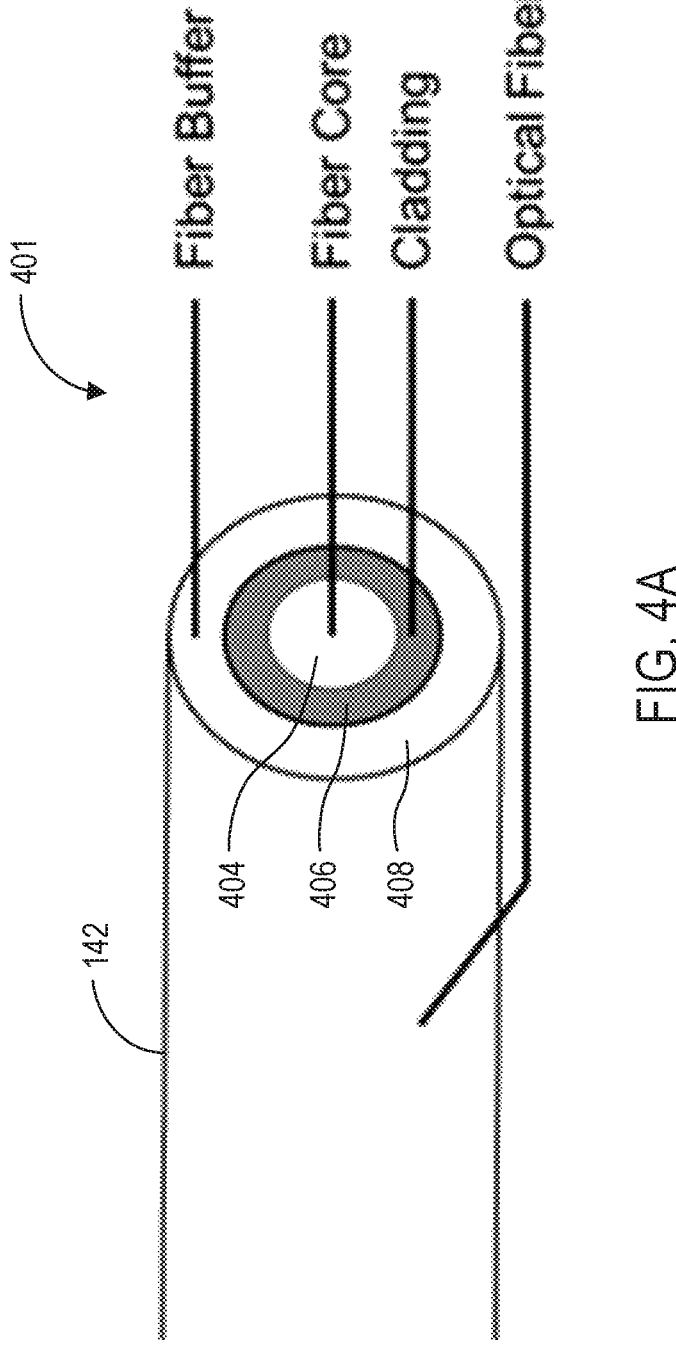
FIGS. 4A-4C show formation of the illumination source at a distal end of the optical fiber.
Figure 4B:
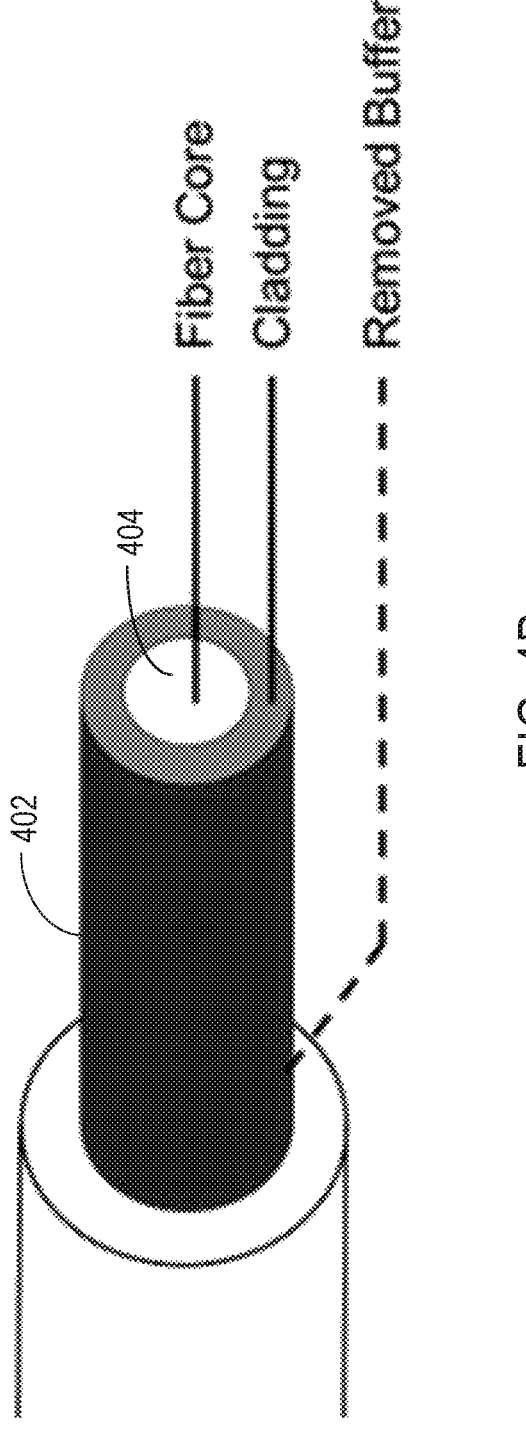
Figure 4C:
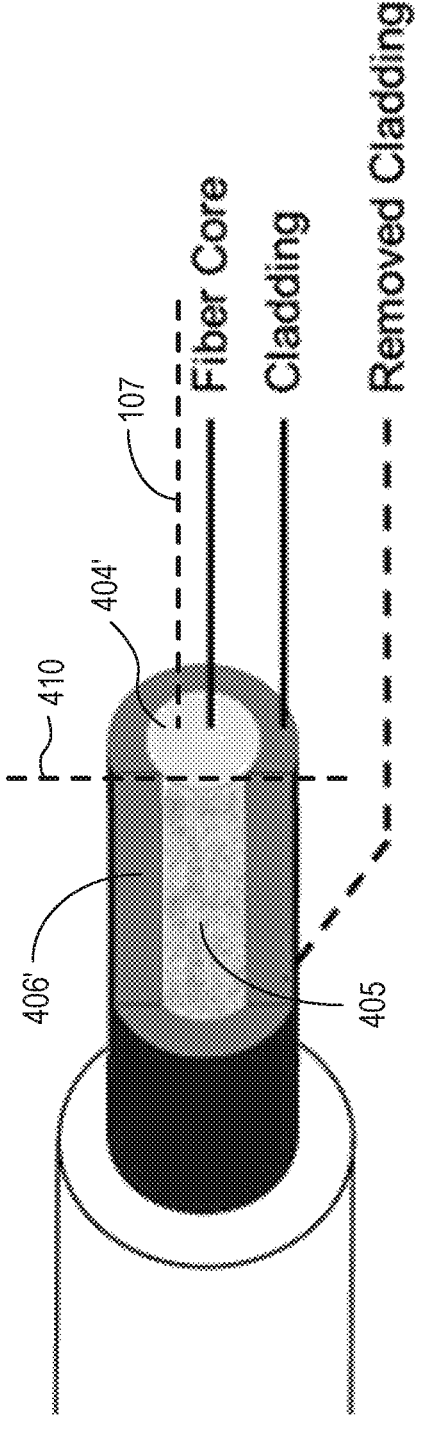

FIGS. 4A-4C show formation of the illumination source 130 at a distal end 401 of the optical fiber 142. Referring to FIGS. 4A-4C, directional side illumination capability for forming the diffusing fiber is achieved through a multimode fiber approach designed for illumination from the linear tip 402, which has a pure silica core 404 with a polymer cladding 406, as depicted in Fig. A. To achieve a wider illumination range from a sidewall of each fiber, a special-ized diffusing process is implemented on the fiber core 404. The fiber buffer 408 was removed initially using a fiber stripper to expose the fiber cladding 406 (FIG. 4B) and then part of the fiber cladding was processed. The cladding on one tangent plane 410 of the fiber's side surface is removed to uncover the fiber core 404, as shown in FIG. 4C. The processed fiber may be etched with glass etching cream for two hours and cleaned with water. As the cladding 406 does not react with the cream, only the exposed part 405 of the fiber core 404' is etched, resulting in light emission in a desired azimuthal direction. The tangential separation or cut forming the plane 410 is slightly off-center, forming a substantially flattened portion of the normally circular cross section of the fiber core 404', with the cladding 406' also removed to form a flush or substantially flush surface. In a typical configuration, between 2-6 cm of side cladding may be removed, forming a 2-6 cm linear illumination source 130.

Returning to the example of FIGS. 1-2B, each of the illumination sources 130 includes an optical fiber extending from the controller, and includes the fiber core 404, and the cladding 406 surrounding the fiber core, where the cladding 406' is removed from a radial section defined by the tangent plane 410 at the distal end 105 of the optical fiber for defining the illumination source. In some configurations, the illumination source 130 may be formed from shaved section defined by removal of a longitudinal segment of the distal end 105 along a line parallel to a fiber axis 107. The optical fibers 142, or diffusion fibers, form the illumination source 130 at the distal end 105 where a linear segment of the core 404' is exposed for diffusing light into the irradiation region 134.

Figure 5:
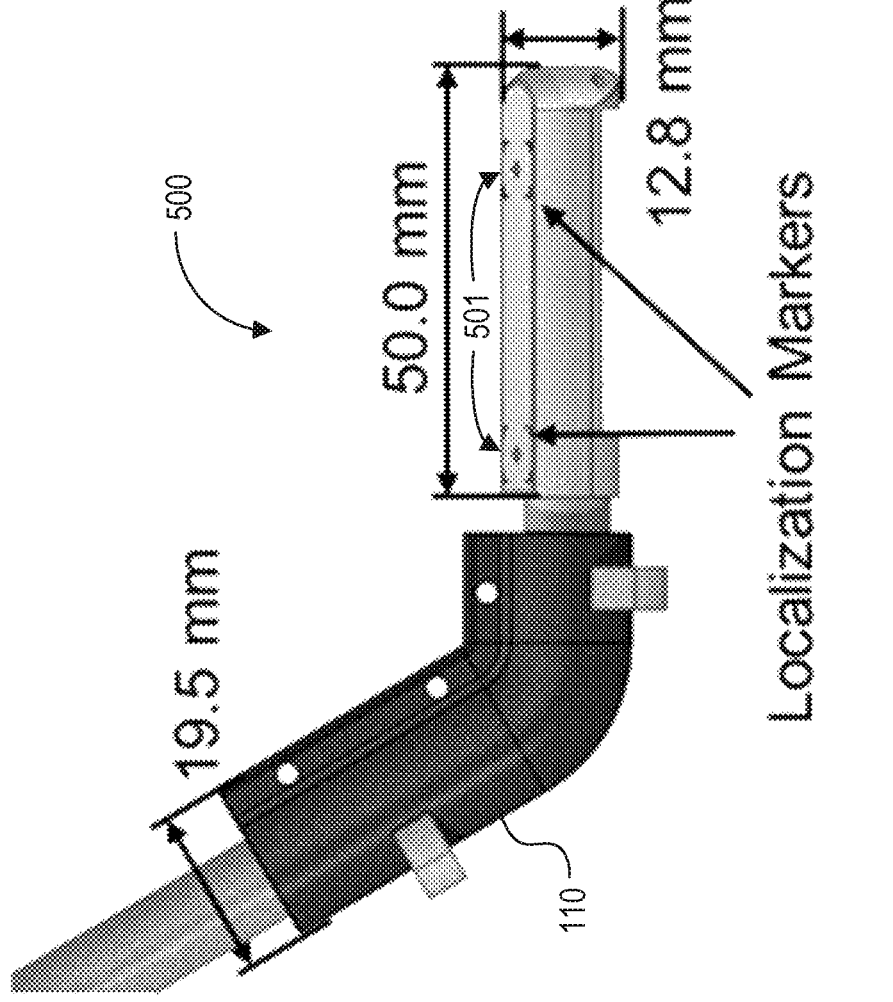
FIG. 5 shows a side view of a laparoscopic probe based on the probe of FIG. 2A.

FIG. 5 shows a side view of a laparoscopic probe 500 based on the probe of FIG. 2A. Referring to FIGS. 1-5, the diffusing fiber illuminated compact photoacoustic (PA) probe 110 may be adapted for seamlessly integration with surgical robots for intraoperative guidance. A robotic inter-face receives the 10 mm diameter of the US probe, as a standard forceps tool has an 8 mm diameter. Markers 501 may be used which enables the localization of the PA probe during imaging and projection of the PA functional infor-mation into the surgical region. Other methods of probe tracking (e.g. robot encoder, electromagnetic tracking sys-tem, etc.) may also be used depending on the application scenario.

Other scenarios include an ablation tip configured for ablation of tissue along the imaging plane, such that the controller 140 is responsive to the ultrasonic sensor 120 for rendering an image on a rendering device indicative of the imaging plane. Necrosis detection and distinction from healthy tissue guides the imaged ablation. A further exten-sion may employ multiplexor connected to the diffusion fibers, such that the diffusion fibers are responsive to the multiplexor for irradiating the surgical region for inducing acoustic signals or emanating ablation signals. The same optical fibers may transmit either laser ablation energy or PA inducing signals, depending on the multiplexed signal.

Figure 6:
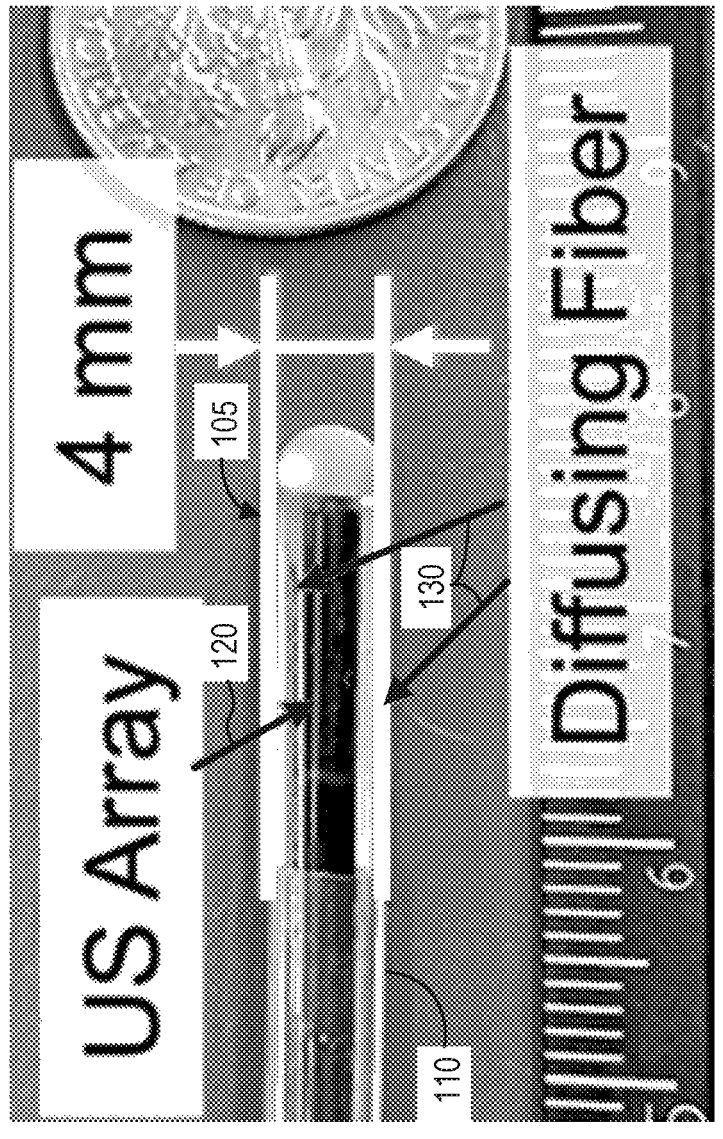
FIG. 6 shows a side view of a catheter probe based on the probe of FIG. 2A.

FIG. 6 shows a side view of a catheter probe based on the probe of FIG. 2A. Referring to FIGS. 1, 2 and 6, the probe 110 encapsulates the photoacoustic bundle 152 at the distal end 105 and connects to the controller 140 at the proximal end 141, such that the probe has a bore containing the diffusion fibers 142 and control conductors (wires) 144 connected to the ultrasonic sensor 120.

The technique of diffusing fiber illumination can also be applied to the US catheter, such as the intracardiac echocar-diography (ICE) probe, to access narrow body channels like vessels and urethral channels and to approach targeted regions. To create the proposed PA catheter, two side-diffusing fibers were affixed to the ICE US catheter, as depicted in FIG. 6. The catheter features two active degree-of-freedom (DoF) bending tips that allow for navigation through the vessel and approach to the heart. The diffusing fibers 142 were arranged parallel to the US sensing array 120, providing illumination throughout the entire imaging area. The various components were secured in place with a customized 3D-printed holder and packaged in a soft silicon tube with an outer diameter of 4 mm. This instrumentation permits physicians PA imaging to navigate through the anatomical structures during surgical guidance and diagnosis.

Figure 7:
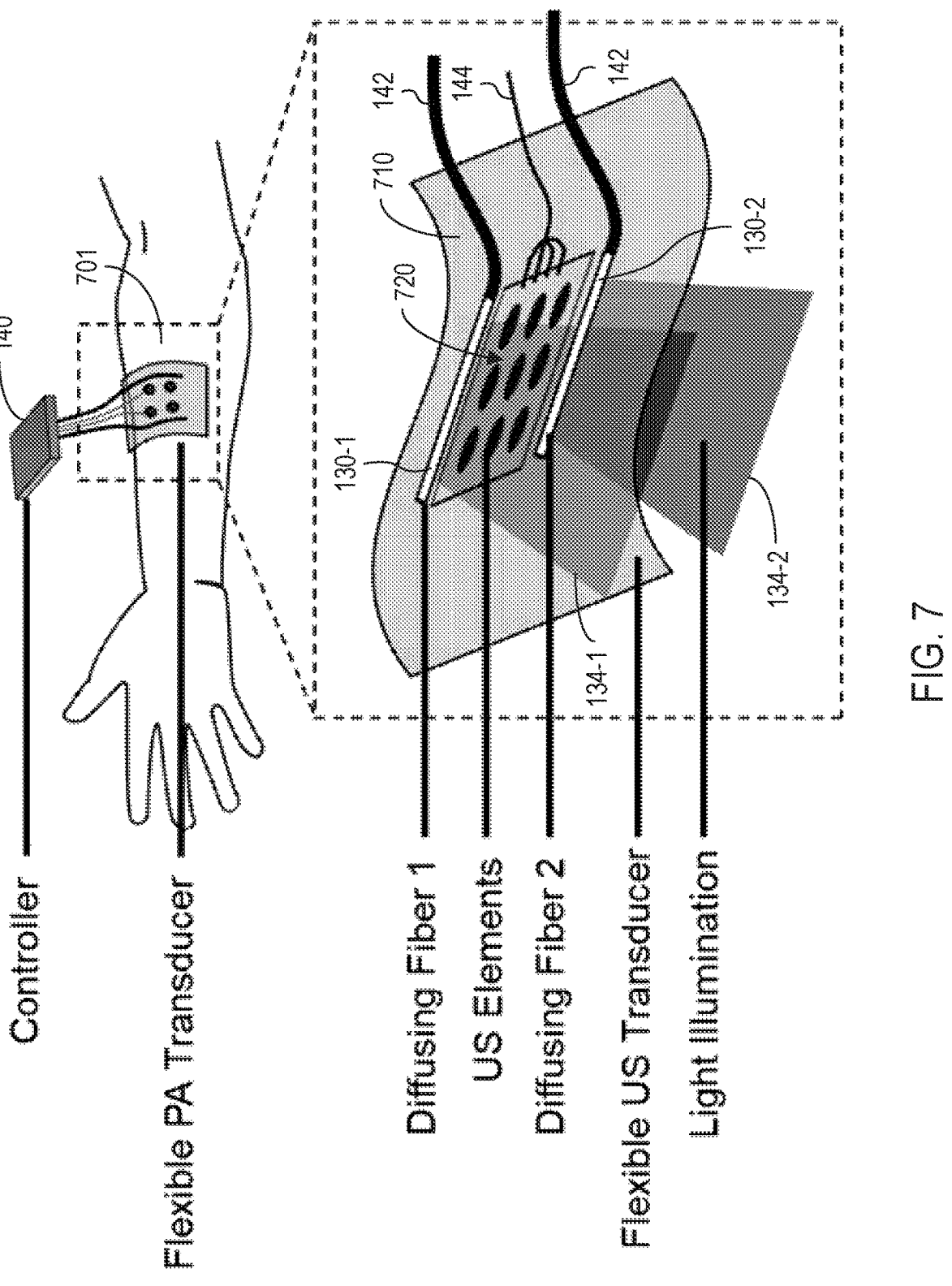
FIG. 7 shows a perspective view of a flexible probe configuration adapted for epidermal deployment.

FIG. 7 shows a perspective view of a flexible probe configuration adapted for epidermal deployment. Referring to FIG. 7, an epidermal usage is shown where the flexural property of the diffusing fiber renders it suitable for use as a flexible sensing patch on the skin 701 as illustrated. The diffusing fiber 142 and illumination source 130 can be effortlessly incorporated onto a flexible sensor array 720 to provide functional PA information. Utilizing the proposed diffusing fiber in this context provides distinctive advantages over other light delivery mechanisms. The bulk of a fiber bundle makes it unsuitable for use as a skin patch 710, while angled-tip illumination fibers cannot illuminate as wide an area as the proposed diffusing fiber. In FIG. 7, the illumination source 130 defines an irradiation region extending from a linear dimension of the illumination source, as the irradiation region intersecting with an imaging plane or region defined by the flexible sensor array 720, such that the ultrasonic sensor 720 is receptive to acoustic signals emanating from the imaging plane or region resulting from the pulsed illumination as above.

Other configuration augment and enhance the disclosed device and example implementation described above. The distinctive feature of localized irradiation from the sensor bundle including both the PA transducer (sensor) in a miniaturized form and close adjacency allows deployment into treatment regions unattainable by conventional approaches. Conventional approaches relying on external illumination sources require substantial power and bulk to penetrate more than a shallow depth into tissue.

A particularly beneficial configuration is a borehole for neurosurgery, often into a skull region. Localized deployment of the illumination source in the borehole is achieved with the disclosed sensor bundle that encapsulates the illumination source and sensory transducer in an internal adjacency in the surgical site defined by the borehole. Such a borehole is often 12-14 mm in diameter, which easily accommodates the sensor bundle and corresponding probe, which occupies only about 4 mm in diameter, in addition to accommodating other instruments or probes such as ablation instruments.

In other configurations, the opening in the skull defined by the borehole can receive illumination is from fibers or other diffuse light sources, such as point sources, directional, cylindrical, or omnidirectional elements that extend down that hole and illuminate the tissue as a depth. Ultrasonic sensing can be provided either near the hole opening (including ring array and acoustic mirror from other related IP) or on an instrument alongside the illumination.

In still other configurations, the sensor bundle may be deployed with an epidermally disposed ring array, such as that disclosed in the copending applications cited above. The surface mounted US array, optionally with a central reflector, complements the sensor bundle when inserted into a borehole or laparoscopic incision for internal surgical regions. The flexible skin patch configuration of FIG. 7 may also be employed in conjunction with the US ring array approach in the copending applications cited above.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A photoacoustic imaging device, comprising: an ultrasonic sensor, the ultrasonic sensor defining a sensing area; at least two illumination sources, each illumination source extending linearly for irradiating a sensing region aligned with the sensing area, each illumination source emanating from a tangentially flattened distal portion of a respective optic fiber; and a controller connected to the illumination sources for pulsed illumination of the illumination sources and corresponding reception of acoustic signals by the ultrasonic sensor.

2. The device of claim 1, wherein the ultrasonic sensor extends longitudinally for defining a linear sensing area; and
   the illumination source extends longitudinally for irradiating the sensing region.

3. The device of claim 2, wherein the illumination source further comprises a plurality of illumination sources, each illumination source of the plurality of illumination sources extending in parallel for defining an intersecting irradiation region emanating from the parallel illumination sources.

4. The device of claim 3, wherein each of the illumination sources includes an optical fiber, the optical fiber extending from the controller, further comprising:
   a fiber core; and
   a cladding surrounding the fiber core, the cladding removed from a radial section at a distal end of the optical fiber for defining the illumination source.

5. The device of claim 4, further comprising a shaved section, the shaved section defined by removal of a longitudinal segment of a distal end along a line parallel to a fiber axis.

6. The device of claim 2, wherein the ultrasonic sensor senses an imaging plane, the imaging plane defined by a region parallel to the linear sensing area and extending perpendicular to the longitudinal extension of the ultrasound sensor.

7. The device of claim 6, wherein the imaging plane resides in an irradiation region resulting from irradiation of light from the illumination source.

8. The device of claim 2, wherein the illumination source defines an irradiation region extending from a linear dimension of the illumination source, the irradiation region intersecting with an imaging plane, the ultrasonic sensor receptive to acoustic signals emanating from the imaging plane resulting from the pulsed illumination.

9. A photoacoustic imaging device, comprising: an ultrasonic sensor, the ultrasonic sensor extending longitudinally for defining a linear sensing area; an illumination source defined by a photoacoustic bundle, the photoacoustic bundle including a plurality of diffusion fibers flanking the ultrasonic sensor and irradiating an irradiation region aligned with the sensing area, each of the diffusion fibers terminating in the respective illumination source, wherein an imaging plane is defined by an intersection of an irradiation region extending from each of the illumination sources and the linear sensing area; and a controller connected to the illumination source for pulsed illumination of the illumination source and corresponding reception of acoustic signals by the ultrasonic sensor.

10. The device of claim 9, further comprising a probe, the probe encapsulating the photoacoustic bundle at a distal end and connecting to the controller at a proximal end, the probe having a bore containing the diffusion fibers and control conductors connected to the ultrasonic sensor.

11. The device of claim 10, wherein the probe is elongated for extension into a surgical region, the imaging plane passing through the surgical region, the ultrasonic sensor responsive to changes in tissue density of the surgical region resulting from at least one of a vasculature, a tumor and necrosis.

12. The device of claim 9, wherein the photoacoustic bundle further comprises an ablation tip, the ablation tip configured for ablation of tissue along the imaging plane, the controller responsive to the ultrasonic sensor for rendering an image on an rendering device indicative of the imaging plane.

13. The device of claim 12, further comprising a multiplexor connected to the diffusion fibers, the diffusion fibers responsive to the multiplexor for irradiating the surgical region for inducing acoustic signals or emanating ablation signals.

14. The device of claim 2, wherein the ultrasonic sensor is a side firing ultrasonic array at a distal end of a probe and aligned with an irradiation region emanating from a plurality of the illumination sources, the side firing ultrasonic array forming a sensing region extending perpendicularly from the probe for forming an image plane based on an intersection of the sensing region and the respective irradiation regions.

15. A method for photoacoustic imaging, comprising:
extending an ultrasonic sensor longitudinally for defining a linear sensing area;
bundling the ultrasonic sensor with at least two illumination sources;
energizing the illumination sources, each illumination source extending longitudinally parallel to the ultrasonic sensor for irradiating a sensing region aligned with the linear sensing area with pulsed illumination, each illumination source emanating from a tangentially flattened distal portion of a respective optic fiber; and
receiving acoustic signals at a controller connected to the ultrasonic sensor.

16. The method of claim 15, further comprising illuminating a plurality of illumination sources, each illumination source of the plurality of illumination sources extending in parallel for defining an intersecting irradiation region emanating from the parallel illumination sources.

17. The method of claim 16, further comprising extending an optical fiber from the controller for defining each of the plurality of illumination sources, each optical fiber including:
a fiber core; and
a cladding surrounding the fiber core,
further comprising removing the cladding from a radial section along a longitudinal segment of the distal end along a line parallel to an axis of each respective optical fiber for defining the respective illumination source.

18. The method of claim 16 further comprising receiving the acoustic signals by the ultrasonic sensor sensing an imaging plane, the imaging plane defined by a region parallel to the linear sensing area and extending perpendicular to the longitudinal extension of the ultrasound sensor.

19. A photoacoustic imaging system, comprising: an ultrasonic sensor, the ultrasonic sensor extending longitudinally along an elongated probe for defining a linear sensing area; at least two illumination sources, each illumination source extending longitudinally adjacent the elongated probe for irradiating a sensing region aligned with the linear sensing area, each illumination source emanating from a tangentially flattened distal portion of a respective optic fiber; and a controller connected to the illumination sources through a bore in the probe for pulsed illumination of the illumination sources and corresponding reception of acoustic signals by the ultrasonic sensor.

20. The system of claim 19 further comprising:
a circular array of transducers, the circular array of transducers defined by a circular frame having the transducers disposed thereon; and
a reflector for redirecting imaging signals between a transducer and an imaged region; wherein
the elongated probe extends through the circular array and aligned with the reflector.

* * * * *